Dec. 18, 1962 P. K. FUJIHARA Plant Pat. 2,202
PEACH TREE
Filed Dec. 16, 1960
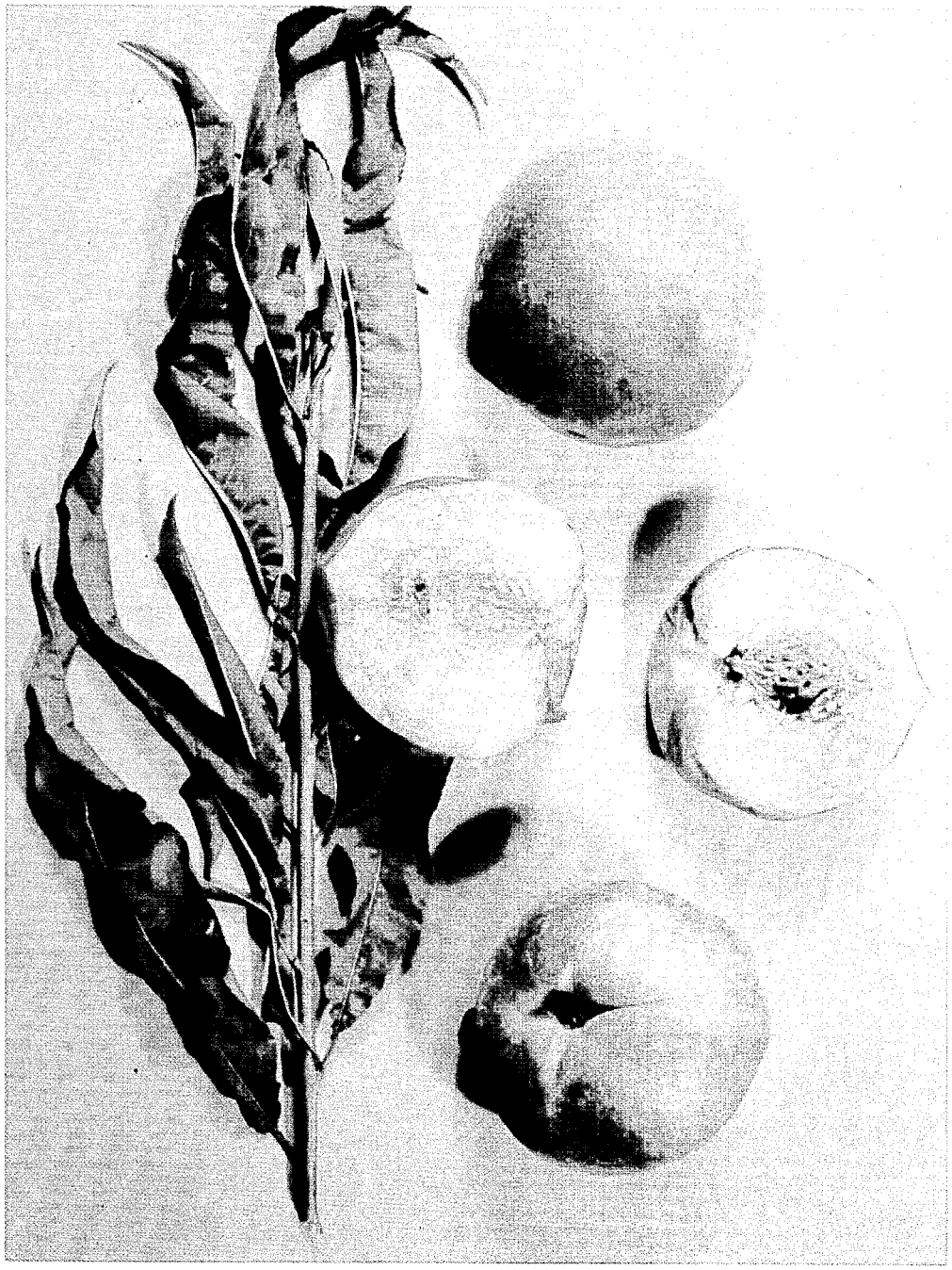
PAUL K. FUJIHARA
INVENTOR
HUEBNER & WORREL
ATTORNEYS
BY Richard M. Worrel United States Patent Office Plant Pat. 2,202
Patented Dec. 18, 1962

2,202
PEACH TREE

Paul K. Fujihara, 10251 E. American, Del Rey, Calif.

Filed Dec. 16, 1960, Ser. No. 76,426
1 Claim. (Cl. 47—52)

The present invention relates to a new and distinct variety of peach tree.

With a view toward developing the subject peach tree, the applicant cross-pollinated a Giant Babcock peach tree (United States Plant Patent No. 1,353) with a Merrill Gem peach tree (United States Plant Patent No. 868), wherein the former served as the female parent and the latter as the male parent. Seeds from the fruit borne by the cross-pollinated tree were planted in 1955, yielding seedling plants. In 1957, scions from the seedling plants were grafted on S-37 rootstock (United States Plant Patent No. 904). Asexual reproduction was thereby successfully accomplished inasmuch as the progeny accurately and consistently possess the distinguishing characteristics of the original seedling trees. The entire development of my subject peach tree including cross-pollination, seed planting, and asexual reproduction, was accomplished by me on my ranch at Del Rey, California, where there is presently a small orchard of the trees of the subject variety.

Because of its known parentage, the present variety is conveniently compared therewith. The most significant characteristics of the fruit of my new peach tree include: a free stone as compared with the cling stone of the Merrill Gem; a relatively early maturity period between June 15 to June 30, thus maturing during about the same period as the Merrill Gem but being two to four weeks earlier than the Giant Babcock; an average size larger than the Giant Babcock but about the same size as large Merrill Gems; improved flavor and taste as compared with the Merrill Gem; juicier than the Merrill Gem; and more firm than either the Merrill Gem or the Giant Babcock. Thus the early maturity and firmness of the subject fruit enable it to be shipped to distant points with minimum deterioration in quality.

The accompanying drawing, which is a dye transfer print of a color photograph, shows typical specimens of the fruit and foliage of the subject peach tree taken shortly after being picked. The colors are as nearly true as is reasonably possible in a color representation of this type.

The following is a detailed description of the characteristics of the subject fruit in accordance with the outline suggested by U. P. Hedrick in his book entitled "Systematic Pomology," published in 1925, and in accordance with the color terminology employed in the "Dictionary of Color" by Maerz and Paul, Second Edition. Where dimensions, sizes, colors, or other characteristics are given, it is to be understood that such characteristics are approximations of averages set forth as accurately as practicable.

Tree: Grows vigorously and trouble free; growth is faster than the Merrill Gem.

*Size, figure and shape.*—Same as the Giant Babcock.

*Productivity.*—Heavy.

*Regularity of bearing.*—Appears to be very regular in that applicant has obtained a relatively big crop every year since 1957 to the present.

*Trunk.*—Similar to the Giant Babcock.

*Branches.*—Size—similar to the Giant Babcock and the Merrill Gem. Surface character—rough and similar to the Giant Babcock. Color—Gray-Green background—Plate 20-E-3; and patches or speckles of Beige—Plate 14-L-5 on the background. Lenticels—in number, less than the Giant Babcock but more than the Merrill Gem; in size, smaller than the Giant Babcock but larger than the Merrill Gem.

*Leaves.*—Size—large, like the Merrill Gem but larger than the Giant Babcock. Length—6⅕ inches. Width—1⅝ inches. Shape and marginal form—approximates the Giant Babcock and Merrill Gem. Color—Green—Plate 21-G-7. Petiole—length—7/16 inch; thickness—5/64 inch. Stem glands—number—mostly two per stem; arrangement—one on each side where present; size—minute; mostly reniform; and color, Burnt Umber—Plate 15-A-12. Stipules—none.

Flower buds: About the same as the Giant Babcock.

Flowers:

*Dates of bloom.*—About the same as the Merrill Gem.

*Size.*—Similar to the Giant Babcock.

*Color.*—Pinkish red like the Giant Babcock.

Fruit:

*Maturity.*—Shipping maturity is from about June 15 to about the end of June.

Size.—Quite uniform; axial diameter—3⅝ inches; transverse diameter in the suture plane—3 inches; and transverse diameter at a right angle to the suture plane—3¼ inches.

*Form.*—Quite uniform; slightly asymmetric; suture—4½ inches long and extending from the stem cavity to the apex; stem cavity—deep and elliptic; base—rounded and curving smoothly into the stem cavity; apex—prominent and pointed; skin—normal thickness, smooth texture, no noticeable tendency to crack, very slight downy fuzz, and color of Reddish Gray— Plate 5-K-7.

*Flesh.*—Color—Ivory, Plate 10-B-2; surface of pit cavity—rough; color of pit well, Pink—Plate 1-K-3; quite juicy; flavor—good with relatively low acid; aroma—very fragrant; texture—crispy; ripening—even; and good eating quality.

*Stone.*—Free stone; size—1¾ inches long by 1 1/16 inches wide in the suture plane by ⅞ inch thick at right-angles to hte suture plane; form—ellipsoidal and slightly asymmetric; base—pointed; ridges—prominent; grooves—deep; color, Clove—Plate 15-C-12; no splitting tendency noticed.

*Use.*—Shipping, eating, and canning.

*Keeping quality.*—Will keep for one month or longer—probably longer than the Giant Babcock.

*Shipping quality.*—A primary characteristic of the subject fruit is its ability to keep well for shipment to distant points.

Having thus described my instant peach tree, I claim:

A new and distinct variety of peach tree, substantially as shown and described herein and especially characterized by: its large, free stone fruit as compared with the smaller Giant Babcock and the cling stone of the Merrill Gem, its relatively early maturity as compared with the Giant Babcock, its firmness and keeping quality as compared with the Merrill Gem and Giant Babcock, thereby enhancing its shipping quality, its improved flavor and taste as compared with the Merrill Gem, and its skin of darker red color than the Giant Babcock.

No references cited.